US006695767B2

(12) United States Patent
Martinez Garcia et al.

(10) Patent No.: US 6,695,767 B2
(45) Date of Patent: Feb. 24, 2004

(54) DEVICE, A PROBE AND A METHOD FOR INTRODUCING AND/OR COLLECTING FLUIDS IN THE INSIDE OF AN ANIMAL UTERUS

(75) Inventors: Emilio Martínez García, Murcia (ES); Juan María Vázquez Rojas, Murcia (ES); Jorge Roca Aleu, Murcia (ES); José Luis Vázquez Rojas, Alicante (ES)

(73) Assignee: Universidad de Murcia, Murcia (ES)

( * ) Notice: Subject to any disclaimer, the term of this patent is extended or adjusted under 35 U.S.C. 154(b) by 0 days.

(21) Appl. No.: 09/957,693

(22) Filed: Sep. 20, 2001

(65) Prior Publication Data

US 2002/0072650 A1 Jun. 13, 2002

Related U.S. Application Data

(63) Continuation-in-part of application No. PCT/ES00/00423, filed on Nov. 3, 2000.

(30) Foreign Application Priority Data

Jan. 20, 2000 (ES) .......................................... 200000114

(51) Int. Cl.[7] ............................ A61B 17/43; S61D 7/00
(52) U.S. Cl. ........................................................ 600/35
(58) Field of Search ............................ 600/33–35, 573, 600/581, 562, 564, 565, 567, 563; 604/170, 53, 55, 96, 280, 49, 54, 165, 171, 169, 264; 128/898

(56) References Cited

U.S. PATENT DOCUMENTS

| | | | | | |
|---|---|---|---|---|---|
| 4,775,362 | A | * | 10/1988 | Kronner | 604/103.05 |
| 5,389,089 | A | * | 2/1995 | Bauer et al. | 604/271 |
| 5,558,636 | A | * | 9/1996 | Li et al. | 604/515 |
| 5,624,399 | A | * | 4/1997 | Ackerman | 604/103.03 |
| 5,916,144 | A | * | 6/1999 | Li et al. | 600/34 |
| 2002/0151765 | A1 | * | 10/2002 | Gil Pascual | 600/35 |
| 2002/0193658 | A1 | * | 12/2002 | Simmet | 600/33 |

* cited by examiner

*Primary Examiner*—Samuel G. Gilbert
(74) *Attorney, Agent, or Firm*—Klauber & Jackson

(57) ABSTRACT

The device comprises a tube or catheter 1 that is introduced into the animal's vagina up to the cervix duct 19; a flexible probe 6 constituted of a first flexible tubular body 7, to allow that the probe, after reaching the distal end of the tube 1, may progress through the cervix duct 19 and thereafter through the cervix horn 22, this structure allowing to carry out a method of introducing a fluid with spermatozoids, embryos or therapeutic solutions to the anterior third of the uterus horn, or to obtain embryos from the anterior portions of the uterus horn, without needing sedation or anesthesia and without disturbing the animal's well-being, the device, the probe and the method being essentially applied to porcine livestock, small ruminants and any other animal species.

45 Claims, 9 Drawing Sheets

B

A

I-I

II-II

I-I

III-III

I-I

IV-IV

DEVICE, A PROBE AND A METHOD FOR INTRODUCING AND/OR COLLECTING FLUIDS IN THE INSIDE OF AN ANIMAL UTERUS

CROSS REFERENCE TO RELATED APPLICATIONS

This application is a Continuation-in-part of application PCT/ES00/00423, filed Nov. 3, 2000, the disclosure of which is incorporated herein in its entirety. Priority is hereby claimed under 35 USC Section 120.

OBJECT AND TECHNICAL FIELD OF THE INVENTION

The present invention refers to a device for introducing and/or collecting, in non-surgical way, fluids that may contain or not, cells in the inside of the uterus of a mammal, the device being able to penetrate through the cervix duct (uterus neck) and to reach the uterus horns, in a simple and quick manner without the need of sedation or anesthesia. The invention further refers to a method of using the device, and to a probe being useful for the device.

The invention is preferably applicable in porcine livestock for introducing a fluid of spermatozoids, embryos or therapeutic solutions into the anterior third of a uterus horn near the uterotubal junction , or for obtaining embryos from the upper portions of the uterus horn, in a sow.

The invention may also be applied to small ruminants such as sheep, goats, and other mammal animal species.

BACKGROUND OF THE INVENTION

For carrying out artificial insemination with a low number of spermatozoids and for performing collection and transfer of embryos, the use of surgical techniques, such as laparotomy, has been well known in the art. These conventional techniques have the inconveniences that they are traumatically invasive and require a high degree of specialization of the veterinarians or insemination specialists, appropriate installations for carrying out the technique, and further imply the potential risks to the animal that are inherent to any surgical intervention.

To avoid these inconveniences, non-surgical systems have been developed. However, these systems have been limited to those species as for example bovine and equine animals, in view that the use thereof does not present difficulties due to the large body volume and anatomic configuration of these species. In other species, as for example in porcine animals or in small ruminants, non-surgical systems have only had a minor implementation due to the difficulties encountered in passing through the cervix duct and reaching deep uterine positions, due to that in these animal species the cervix duct has a series of protuberances that render introduction of a probe considerably difficult. This circumstance has hindered practical application of embryo transfer and has limited artificial insemination to the deposition of semen samples to deep vaginal or to cervix level and always requiring a high amount of spermatozoids. Practical application of other biotechniques such as cryopreservation of sperms, preselection of the sex by sperm separation, embryo micromanipulation etc. has been limited by this circumstance.

Specifically in the porcine species, attempts have been made to develop no-surgical rigid systems aimed to pass through the cervical canal and to reach the uterus. Some of these systems comprise a device including a tube or catheter having a proximal end which includes a widened portion for simplifying handling thereof, and the outer surface of the distal end of which includes a spiral portion that permits its introduction and fixing of the device within the entry of the cervix duct and to thereby reach the uterus body. Through the inside of the tube, a probe is introduced. Due to the configuration, these known devices do normally not penetrate further than into the initial portion of the uterus horns.

These devices can only be introduced with difficulties without harming the protuberances of the cervix duct. Moreover they may perforate the wall of the cervix or of the uterus. Such known systems are described for example in WO-A-9714365, U.S. Pat. No. 5,916,144 and WO-A-9927868.

DESCRIPTION OF THE INVENTION

To solve the aforestated inconveniences, the present invention refers to a new device and method that allow, without the need of sedation or anesthesia of the animal, to introduce a fluid with spermatozoids, embryos or therapeutic solutions into the anterior third portion of a uterus horn near the uterotubal junction or which, according to an embodiment thereof allows to collect embryos from the upper portions of the uterus horn.

For this purpose, the device of the invention, the same as the conventional ones, comprises a tube or catheter having a proximal end which includes a widened portion for simplifying handling of the device, and a distal end having an outer surface that includes a spiral portion that enables introduction and fixing of the tube within the entry of the cervix duct, and a probe slidably housed within the tube.

In accordance with the invention the probe is comprised of a flexible tubular body comprising a longitudinal chamber, and at least one flexible duct within the longitudinal chamber in the flexible tubular body, the outside of the flexible tubular body being of a flexible material of plastic or of any other flexible material having an outer surface that allows the probe to slide within the female reproduction apparatus without causing any harm to the mucous membranes. This structure allows the probe to be inserted through the proximal end of the tube, and to be pushed towards the distal end of the tube so that, after it has reached said distal end, it emerges therefrom such that it first advances through the cervix duct and then enters the uterus horn.

Another feature of the invention resides in the fact that connecting means for connecting a tap having at least one way are provided at the proximal end of the probe, said connecting means for enabling introduction and/or collection of fluids.

According to the invention, the probe has a consistency and a resilience being sufficient to allow that, after emerging from the distal end of the tube, it may progress through the cervix duct and through the uterus horn. Thus, in accordance with the invention, the probe has a relationship resilience (=elasticity)/consistency (=stiffness) such that, a longitudinal section of 5 cm length of the probe is able to bend 30° to 160°, particularly 100° to 150°, preferably 135° to 145° and particularly 140°, and such that a longitudinal section of 8 to 10 cm length of the probe resists a load of 1.5 to 4.5N, particularly of about 3N, without bending when the load is applied perpendicularly on the longitudinal section i.e. it has an axial penetration strength of 15 to 45N, particularly about 3N, for a longitudinal section of 10 cm before starting to bend.

In one embodiment of the probe, the flexible tubular body is made of a plastic material as for example a polymer or copolymer such as thermoplastic polyolefin, elastomer, propylene copolymers and other conventional suitable plastic materials which, at the required thickness of the wall of the flexible tubular body, may comply of the aforementioned relationship resilience/consistency.

In another embodiment of the probe, the flexible tubular body is made of a flexible plastic material of the aforementioned type which, however, as such has a higher resilience and/or a lower consistency than those of the hereinabove mentioned the relationship resilience/consistency at the required thickness of the wall of the flexible tubular body, so that the flexible tubular body requires stiffening by alien elements. For this purpose a plurality of flexible longitudinal ribs may be arranged in the longitudinal chamber between the flexible duct and the tubular body, to thereby increase the consistency and to maintain the required resilience of the probe. In an embodiment of the invention, the longitudinal ribs are comprised of steel threads and the longitudinal chamber that includes the steel threads is tubular.

In still another embodiment of the probe, the flexible tubular body is comprised of a helicoidal member such as a spring, made of metal or plastic, the outside of which is covered by a layer of flexible plastic material that allows the probe to slide within the female reproduction apparatus without causing any harm to the mucous membranes of the uterus duct and of the uterus horns.

In still a further embodiment of the probe, the flexible tubular body is comprised of a tubular member of a material such as a plastic or metal, the outer surface of which, as such is insufficiently smooth for sliding within the female reproduction apparatus, and the outside of which is covered by a layer of flexible plastic material that allows the probe to slide within the female reproduction apparatus without causing any harm to the mucous membranes of the uterus body and of the uterus horns.

The distal end of the probe comprises a piece that adapts to the inner space of the flexible tubular body, the piece including an opening that is arranged in axial continuation of the flexible duct for establishing an inlet and/or outlet for the fluids. So as to avoid harm to the mucous membranes, the end of said piece must be smooth and stump.

The coupling means for coupling the tap to proximal end of the probe may be comprised of a piece that, at one end is adapted to the inner space of the flexible tubular body and the flexible duct and, at the other end, is adapted to the tab, so as to allow introduction-extraction of fluids.

In an embodiment of the invention, the probe has two flexible, preferably concentric ducts, one of which, preferably the outer one and in proximity to the distal end of the probe, communicates with an elastic small external coating so that, once the probe has been placed in the uterus horn, the elastic small external coating can be inflated with air through the outer flexible duct so that it swells in a balloon-like manner and thus adapts itself to the wall of the uterus horn thereby preventing a possible reflux through the uterus horn of liquids that have been introduced into the uterus horn, when intrauterine fluids containing embryos are suctioned.

In a preferred embodiment of the invention, the flexible duct communicating with the flexible small external coating, is the longitudinal chamber that includes the longitudinal flexible ribs between which passage of the air towards the flexible small external coating is allowed.

The invention also refers to a method for non-surgical introduction of fluids containing spermatozoids, embryos or therapeutic solutions into the anterior third of a uterus horn or for collecting embryos from the anterior third of the uterus horn of a female mammal by using the afore described device, without the need of sedating the animal and without disturbing its well-being, the method comprising introducing the tube into the inside of the vagina up to the entry of the cervix duct at which point the tube is rotated in a counterclockwise sense, for producing its advance within the cervix duct of the female animal such that it becomes firmly fixed within the walls thereof, once fixing has been achieved, inserting the distal end of the flexible probe by the proximal end of the tube until reaching the anterior end of the tube that is anchored in the inside of the of the cervix duct, slightly rotating the tube to the left and right, and simultaneously pushing the flexible probe until it bypasses the first protuberance of the cervix cavity, further pushing the flexible probe thereby noting that the flexible probe first advances with some difficulty by the various protuberances of the cervix duct until reaching the uterus body, whereby, once the cervix duct has been overcome, the resistance offered by the protuberances ceases, and the flexible probe advances without difficulty until reaching the upper portions of a uterus horn, and, once the flexible probe has been introduced into its final position within the uterus horn, injecting or absorbing fluids into or from the uterine environment through the flexible duct by means of a syringe or a similar device coupled to the tap.

In the case that embryos are to be extracted from the uterus, the method further comprises a subsequent step to introducing the probe into the uterus horn, in which step the elastic small external coating is inflated, whereby the coating adapts itself to the inner space of the uterus horn, and thereafter embryos are suctioned from the anterior portion of the uterus horn.

Thus, the device and method of the invention do not require sedation nor anesthesia of the animal as for example a sow. Furthermore, it does not cause any harm to the well-being of the animal, as it does not use any rigid instrument that might harm and/or perforate the walls of the cervix duct, due to that the flexible probe presents a suitable equilibrium between consistency and resilience for passing the cervix duct and reaching the anterior third of a uterus horn without producing apparent damages.

Additionally, the invention has the great advantage that complete introduction of the flexible probe may be achieved in a minimum time (approximately 3 or 4 minutes) and it allows to work with reduced volumes of semen, embryos or therapeutic solutions, at the same time that it is multifunctional in view that it enables introduction of spermatozoids, embryos and therapeutic solutions deep into the uterus, as well as collection of embryos from the anterior portions of the uterus horn.

BRIEF DESCRIPTION OF THE DRAWINGS

Hereafter, to facilitate a better understanding of the present description and being an integral part thereof, there is accompanied a series of figures in which the subject matter of the invention is represented in an illustrative and non-limiting way.

DETAILED DESCRIPTION OF THE INVENTION

Figure 1:
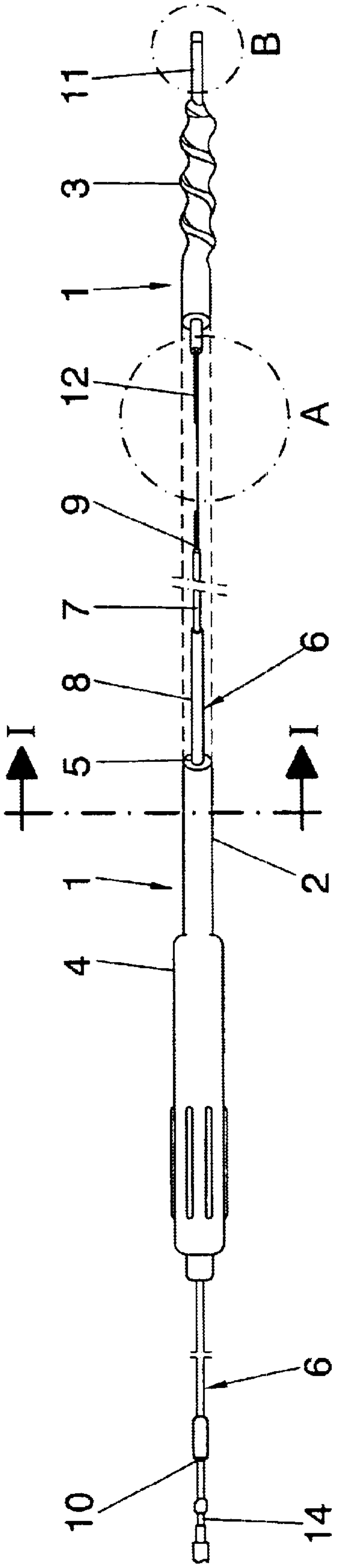
FIG. 1 is a raised side view of the device of the invention in which the probe is inside the tube or catheter, and wherein different sections have been made so as to show the various components that constitute the probe.

A description of the invention will be made on the grounds of the previously mentioned figures. In the figures, there are reference numerals having the following meanings:

1 tube
2 smooth section
3 spiral portion
4 widened portion
5 axial channel
6 probe
7 flexible tubular body (first embodiment)
7*a* outer surface of flexible tubular body
7' flexible tubular body (second embodiment)
7" flexible tubular body (third embodiment)
8 flexible layer
9 longitudinal chamber
10 proximal end of the probe
11 distal end of the probe
12 flexible duct
13 steel threads
14 device at the proximal end of the probe
15 device at the distal end of the probe
16 proximal end portion of device 15
17 distal end portion of device 15
18 distal end of cervix duct
19 cervix duct
20 protuberances on cervix duct walls
21 uterus body
22 uterine horn
23 spirals of uterus horn
24 flexible probe (fourth embodiment)
25 proximal end of probe 24
26 device at distal end of probe 24
27 flexible duct
28 inflatable elastic external coating
29 additional flexible duct
30 tip of flexible probe 24
31 openings in the additional flexible duct 29
32 tap
33 first way of tap 32
34 second way of tap 32
35 syringe In accordance with the invention shown in FIG. 1 the device comprises a tube 1 which includes a spiral 3 portion at the outer surface of its distal end the spiral portion 3 for facilitating insertion and fixing of the tube 1 in the cervix duct 19, and the proximal end of which includes a widened portion 4 for facilitating handling of the tube 1. Between the ends of the tube 1, there is provided a tubular smooth section 2.

Internally, the tube comprises an axial channel 5 that communicates both ends of the tube 1 and that has a sufficiently wide diameter as to allow passage of a flexible probe 6 without any difficulty. Each of the ends of the tube may be made of a single piece of rubber or plastic, or it may be constituted by a molded plastic part, taking into account that the distal end must be smooth so as to avoid damages to the animal when the distal end is introduced into the cervix duct.

Figure 2:
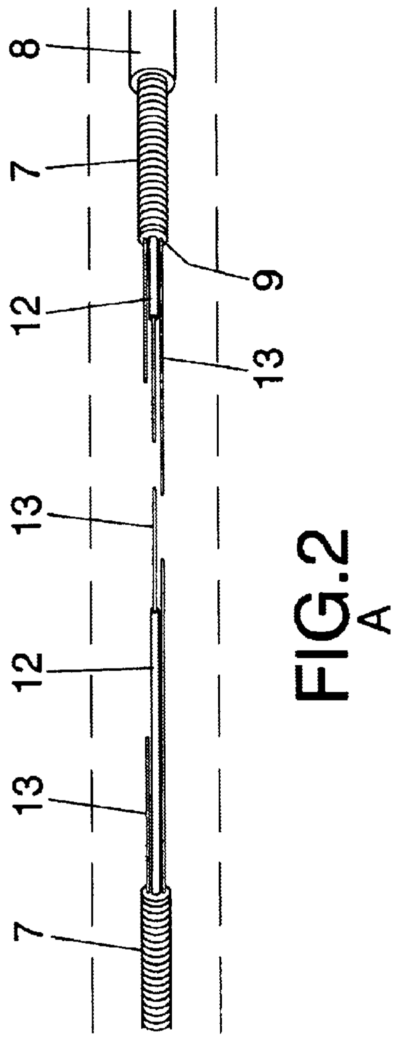
FIG. 2 shows detail A of the preceding figure.
Figure 6:
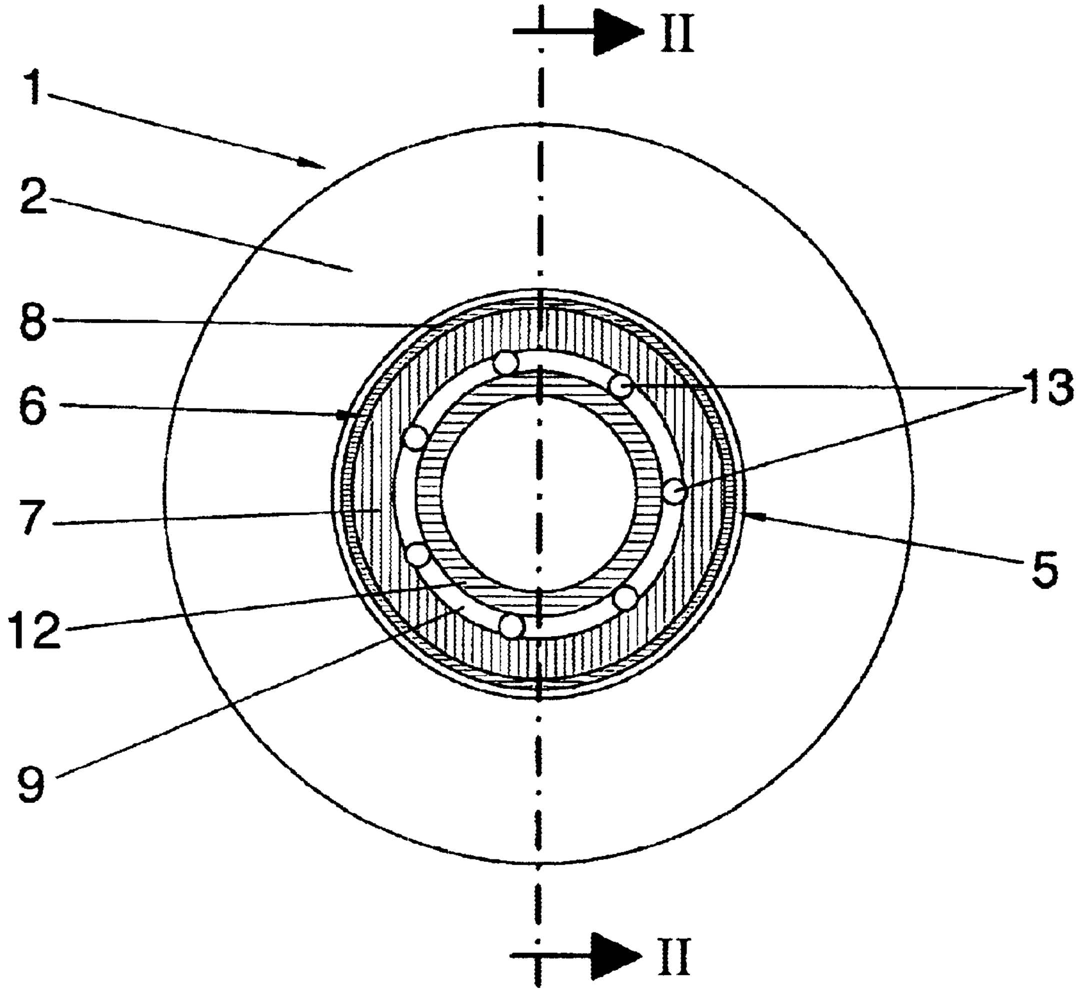
FIG. 6 is a cross sectional view at line I—I in FIG. 1 of the device comprising a probe in accordance with the first embodiment of the probe shown in FIG. 2.
Figure 7:
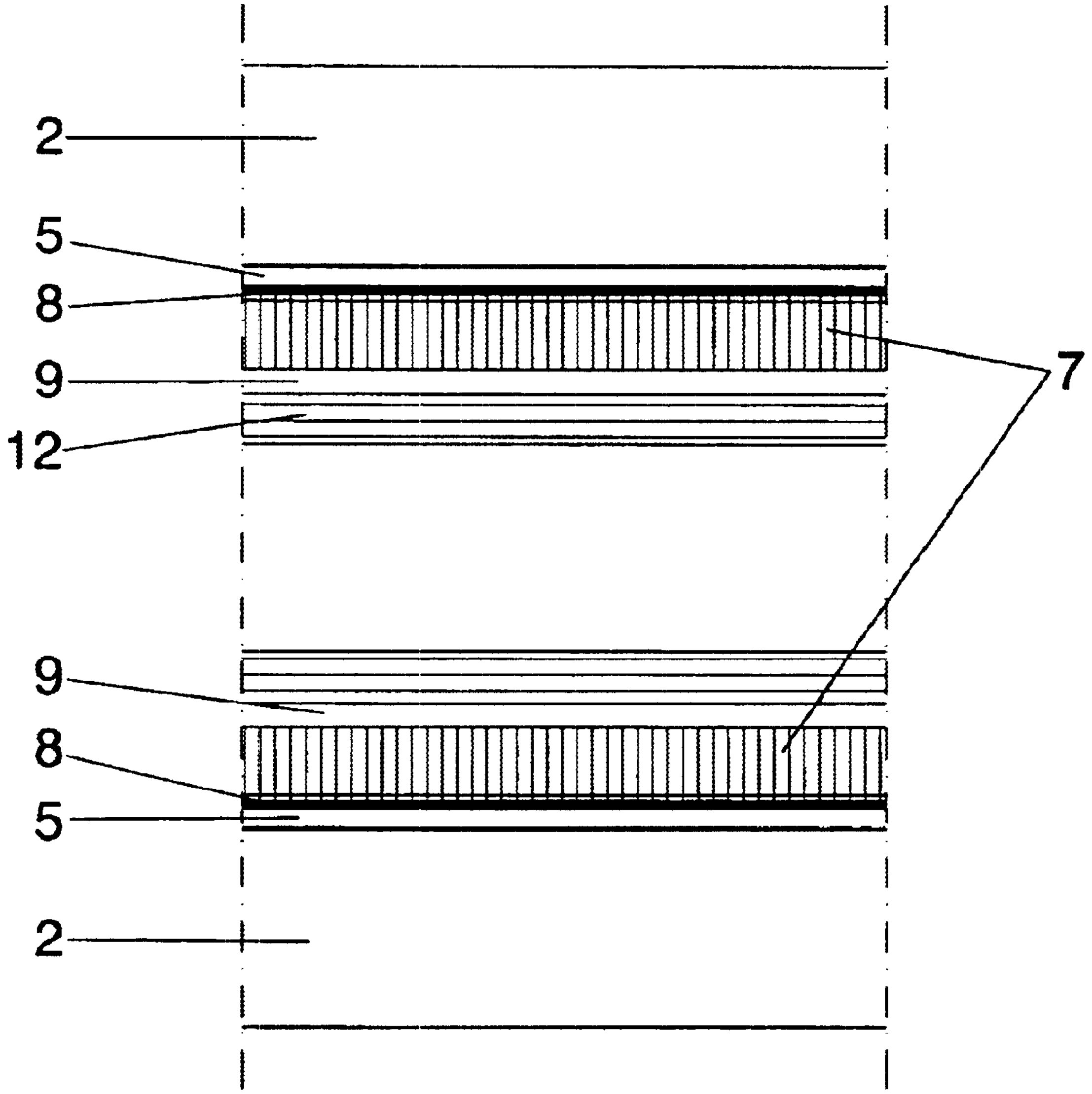
FIG. 7 is a sectional view at the line II—II in FIG. 6.

The first embodiment of the flexible probe 6 shown in FIGS. 2, 6 and 7, comprises a flexible tubular body 7 of plastic. The external surface of the flexible tubular body 7 is covered by a flexible layer 8 of plastic or of any other flexible material that allows sliding of the probe through the female reproduction apparatus without causing any damage to the mucous membranes thereof.

Figure 8:
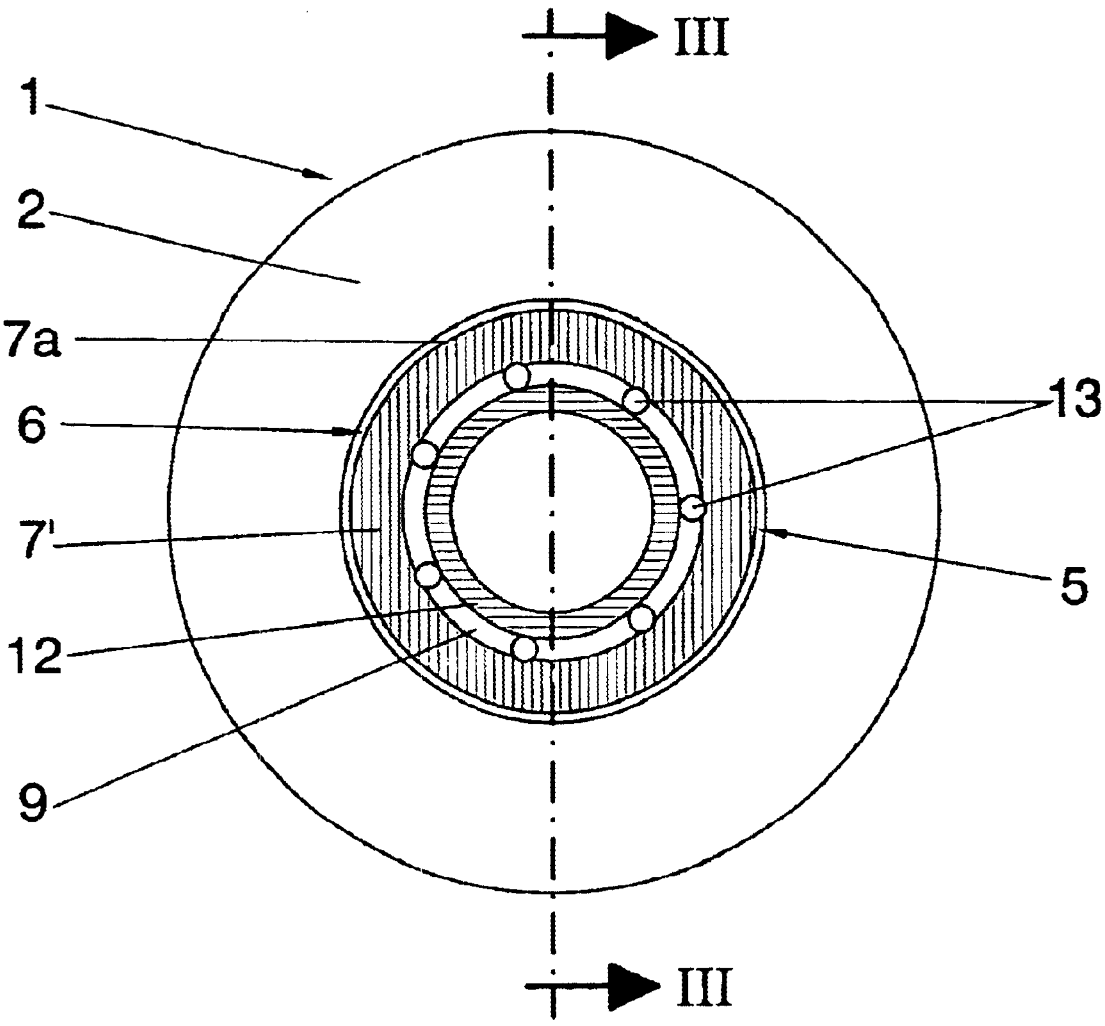
FIG. 8 is a cross sectional view at line I—I in FIG. 1 of the device comprising a probe in accordance with a second embodiment.
Figure 9:
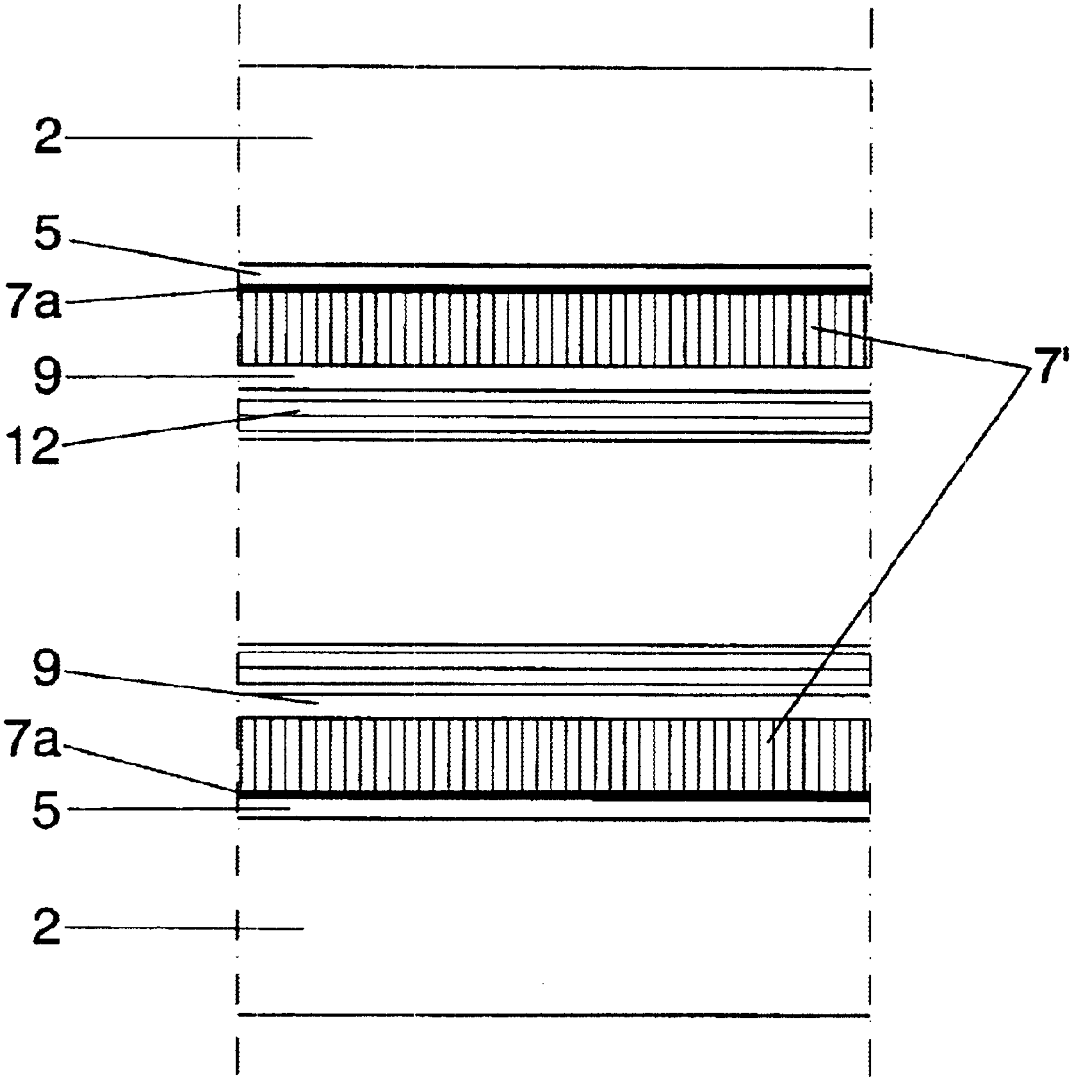
FIG. 9 is a sectional view at line III—III in FIG. 8.

In the second embodiment of the flexible probe 6 shown in FIGS. 8 and 9, the flexible tubular body 7' is made of a plastic material having an outer surface that allows sliding of the probe through the female reproduction apparatus without causing any damage to the mucous membranes.

Figure 5:
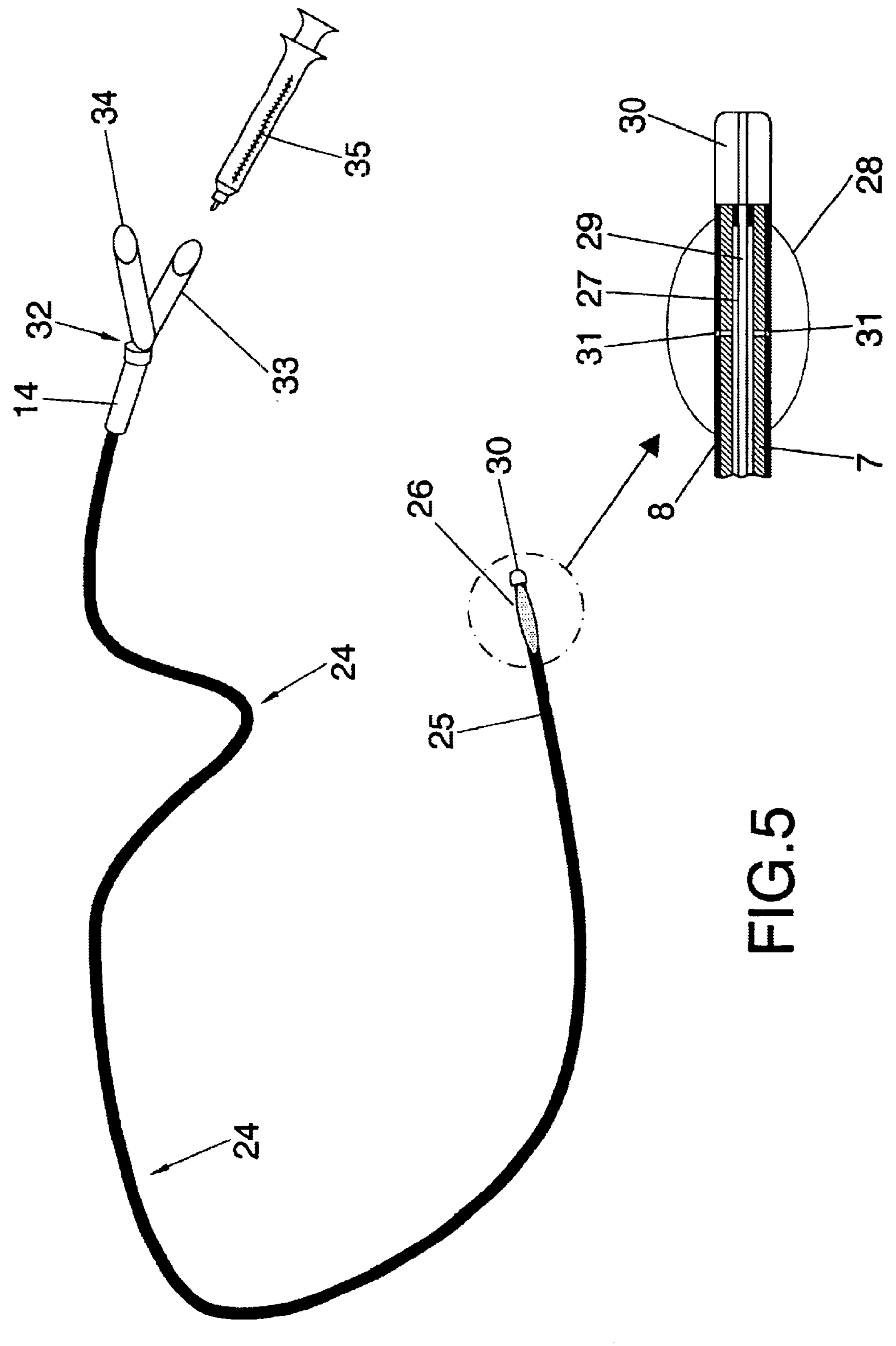
FIG. 5 is a schematic representation of an example of an embodiment of the flexible probe of the invention used for obtaining embryos from the anterior third of a uterus horn, this figure also showing details of the distal end of the probe.
Figure 10:
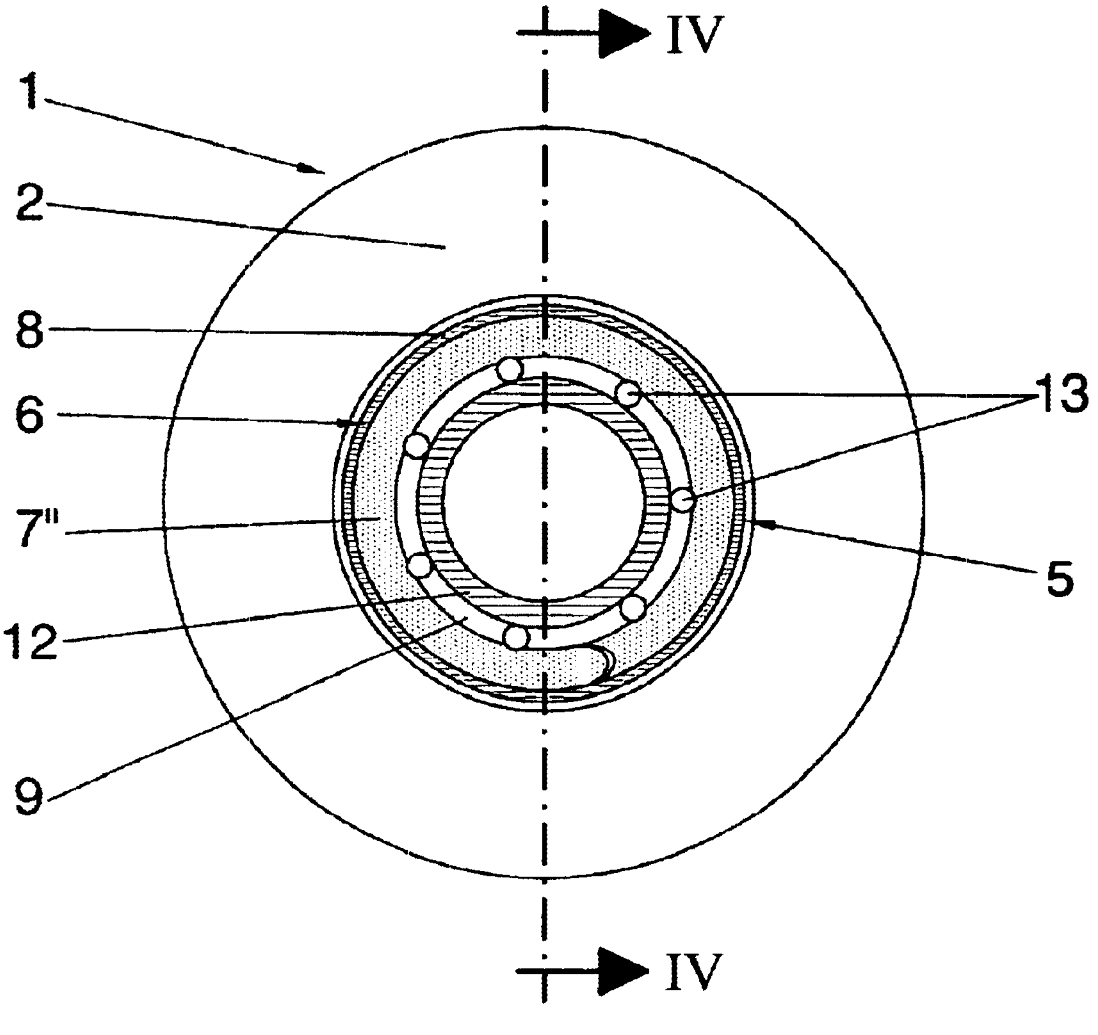
FIG. 10 is a cross sectional view at line I—I in FIG. 1 of the device comprising a probe in accordance with a third embodiment.
Figure 11:
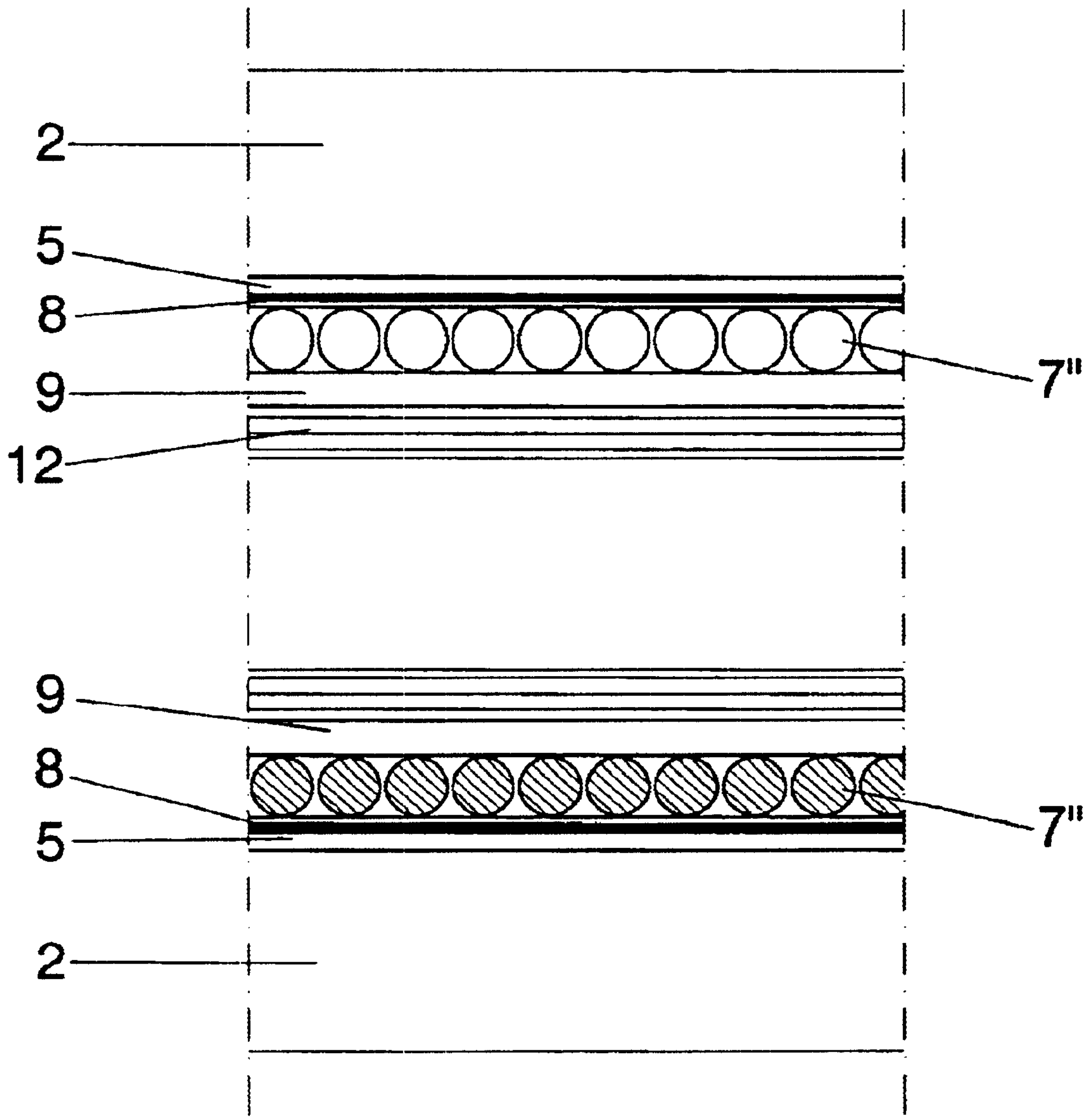
FIG. 11 is a sectional view at line IV—IV in FIG. 10.

The third embodiment of the probe 6 shown in FIGS. 10 and 11, comprises a flexible tubular body 7" made of an helicoidal member the outside of which is covered by a layer 8 having the same characteristics in respect of its outer surface as the layer described hereinbefore with reference to FIGS. 5 and 6.

In any of the afore described embodiments of the probe 6, in the inside of the flexible tubular body 7, a flexible duct 12 of silicone or another similar material is provided, whereby a longitudinal chamber 9 extending from the proximal end 10 to the distal end 11 is formed between said flexible duct 12 and the flexible tubular body 7.

As shown in FIG. 2, a plurality of steel threads 13 is axially arranged inside the longitudinal chamber 9, the steel threads being intended to increase the consistency of the probe.

The proximal end 10 of the probe 6 is formed of a device 14 of plastic or of another material, that enables coupling with the flexible tubular body 7 and with the flexible duct 12 by one of its ends, and by its other end enables coupling, as shown in FIG. 5, with a tap 32 of one or two ways 33,34.

Figure 3:
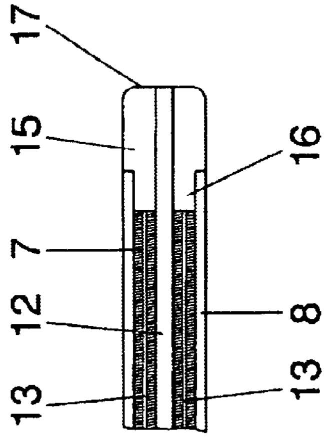
FIG. 3 shows detail B of FIG. 1.

As shown in FIG. 3, the distal end 11 of the probe 6 is formed of a device 15 of methacrylate, plastic, metal or any other material. The device 15 is inserted into the inner space of the flexible tubular body 7 by its proximal end portion 16, whilst its distal end portion 17 communicates with the outside through a hole that constitutes the fluid inlet and/or outlet that is a continuation of said flexible duct 12. Said distal end 17 must be smooth and stump to avoid harms to the animal's mucous membranes.

To prevent contaminations, the device of the invention may be suitably sterilized and packaged in hermetically sealed bags.

Figure 4:
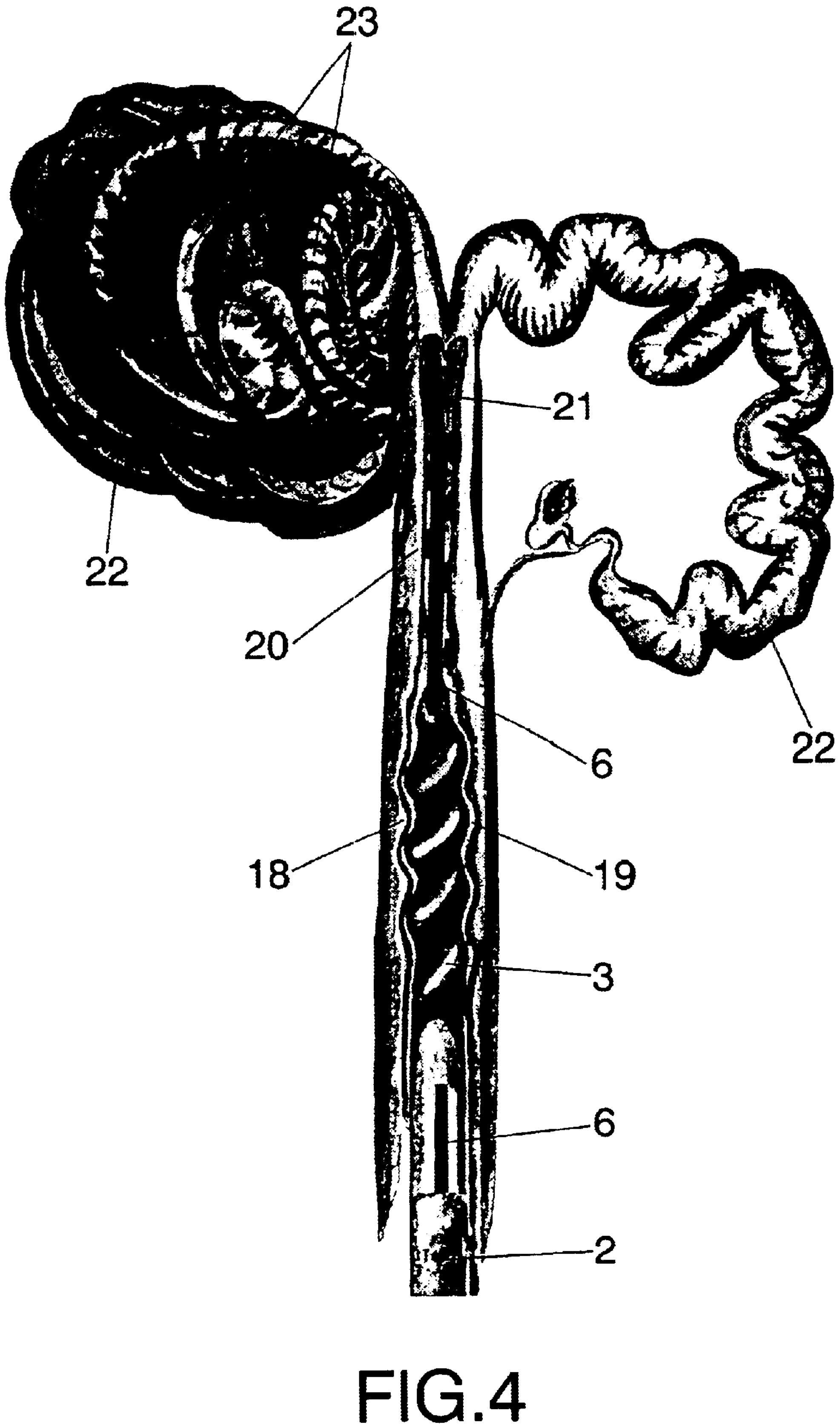
FIG. 4 is a schematic representation of the device of the invention in an operating situation within the uterus of a sow.

In the following, the method of using the device as hereinabove described with reference to FIG. 1 for profound intrauterine insemination of a sow with a low amount of spermatozoids will be described with further reference to FIG. 4.

The method of the invention comprises introducing the tube 1 up to the inside of the cervix duct of the sow in high estrus which may have superovulated or not. For this purpose, a non-toxic lubricant liquid is applied onto the tube 1 so as to facilitate passage thereof through the vagina. The tube 1 is inserted by introducing its distal end (area of the spiral portion 3) into and through the sow's vagina until reaching the distal end 18 of the cervix duct 19. In that moment, the tube 1 is rotated in a counterclockwise sense whereby the spiral portion 3 advances within the female animal's cervix duct 19 and becomes fixed between the walls of the cervix duct. As shown in FIG. 4, the walls of the cervix duct are formed of thick rounded protuberances 20. In this situation, as the tube 1 is held from the outside, the uterus neck is firmly held so as to prevent ruptures thereof. Once firm holding of the uterus neck has been established, the distal end 11 of the flexible probe 6 is introduced through the proximal end of the tube 1 and pushed until it reaches the distal end of the tube in the inside of the cervix duct 19. At this position, it can be noted that the flexible probe 6 does not progress anymore. In this moment, the tube 1 is slightly rotated to the left and right, and the flexible probe 6 is simultaneously pushed further until it overcomes the first protuberance 20 of the cervix duct 19. Subsequently, the flexible probe 6 is still further pushed whereby it can be noticed how the probe 6 surpasses, overcoming some resistance, the various protuberances 20 of the cervix duct 19 until reaching the uterus body 21. Once the cervix duct 19 has been trespassed, the resistance offered by the cervix protuberances 20 ceases and the flexible probe 6 advances smoothly, without any difficulty, until reaching the anterior portion of a uterus horn 22. When the flexible probe 6 advances within the uterus horn 22 it bends and thus follows the spiral path 23 of the uterus horn 22. Although it is not absolutely necessary, introduction of small volumes of diluent through the flexible duct 12 will facilitate progression of the flexible probe 6 at its passage through the cervix duct 19 and its progression through the uterus horn 22. Once the flexible probe 6 has been introduced up to its final position within the uterine horn 22, the semen contained in a syringe 35 (cf. FIG. 5) being connected to the proximal end 10 of the flexible probe 6, is introduced through the flexible duct 12 of the flexible probe 6 until it becomes released within the uterine environment. So as to avoid losses of spermatozoids and securing that the semen sample has been completely evacuated from the flexible duct 12, a small volume of diluent is subsequently introduced through the flexible duct 12. Thereafter, the flexible probe 6 which is extracted without any difficulty, is withdrawn and the tube 1 is withdrawn for which this latter must be rotated in a clockwise sense.

This process may also be used for transferring embryos into a uterus horn.

Basically the same device and method may be used for obtaining embryos from the inside of a uterus horn for which purpose a flexible probe 24 as represented in FIG. 5 has been provided. The flexible probe 24 shown in FIG. 5 is similar to the flexible probe 6 described herein with reference to FIG. 2 and 6–11 with the difference that probe 24 has two flexible, concentrically arranged ducts 27 and 29 in its inside, whereby, in the proximity of the distal end 25 of the probe 24, there is a device 25 comprising an elastic small outer coating 28 of latex or silicone communicating with the flexible duct 27 through a hole 31. In this case, the proximal ends of the flexible ducts 27,29 are connected to a two-way tap 32 comprising a first way 33 connected to the flexible duct 29 and a second way 34 connected to the flexible duct 27, so that the previously described methodology is also completely valid in this case, with the only difference that once the flexible probe 24 has been introduced into the anterior third of a uterus horn, the elastic outer coating 28, is filled with air by means of a syringe 35 connected to the flexible duct 27 so that inflation thereof is produced whereby it completely adapts itself to the uterus wall so as to avoid any possibility of a reflux. Thereafter, the embryo culturing medium is introduced through the flexible duct 29, so as to fill the portion comprised between the tip 30 (equivalent to device 15 shown in FIG. 3) of the flexible probe 24 and the uterotubal junction, a place where embryos should be found after 4 to 5 days after insemination of the female animal, with liquid. Afterwards, through the same working channel 29, a suction is applied to recover the liquid that has been introduced and which contains the embryos. This process is repeated until it has been possible to obtain the embryos.

In a preferred embodiment of the invention, the flexible tube 27 is established by the chamber 9 in which the steel threads 13 are included, in which case the air circulates between said steel threads. Thereby, the structure of the probe is simplified.

What is claimed is:

1. A device for introducing and/or collecting fluids in the inside of the uterus of an animal, the device for being introduced through a vagina, an entry of a cervix duct, and the cervix duct into a uterus horn of a uterus body, and comprising a tube having a proximal end and a distal end, and a probe axially and slidably extending through the tube, wherein the probe has a proximal end and a distal end, and comprises a flexible tubular body, at least one flexible duct having an inner space and fixedly housed inside the flexible tubular body, the flexible duct extending through a longitudinal chamber within the flexible body, and an outer smooth surface, the probe having an equilibrium between consistency and resilience such that, when being pushed after emerging from the distal end of the tube, the distal end of the flexible probe advances first through the cervix duct and thereafter through the uterus horn.

2. A device according to claim 1, wherein the probe comprises coupling means for coupling a tap, the coupling means being provided at the proximal end of the probe for at least one of introducing and collecting fluids.

3. A device according to claim 1, wherein the proximal end of the tube comprises a widened portion to facilitate handling of the device.

4. A device according to claim 1, wherein the distal end of the tube has an external surface comprising a spiral portion that facilitates introduction and fixing of the tube in the entry of the cervix duct.

5. A device according to claim 1, wherein, between the flexible duct and the flexible tubular body of the probe, a plurality of flexible longitudinal ribs is arranged for increasing consistency and maintaining flexibility of the probe.

6. A device according to claim 5, wherein the flexible longitudinal ribs are steel threads.

7. A device according to claim 5, wherein the longitudinal chamber is tubular.

8. A device according to claim 1, wherein the distal end of the probe comprises a distal piece that adapted to the inner space of the flexible tubular body and to the flexible duct, the distal piece including an opening being located as a continuation of the flexible duct for establishing at least one of an inlet and an outlet for the fluid.

9. A device according to claim 1, wherein the probe comprises coupling means for coupling a tap, the coupling means being is a proximal piece connected to the inner space of the flexible tubular body, to the flexible duct and to the tap.

10. A device according to claim 1, wherein the probe comprises said flexible duct as a first flexible duct, an additional flexible duct as a second flexible duct within the probe, an elastic small external coating provided on the outside of the probe at a portion near said distal end of the probe, and a communication between the second flexible duct and said outside of the probe, provided in said area near to the distal end of the probe, said external coating and said communication being arranged such that, when the distal end of the flexible probe has been placed in a final position in the uterus horn and air is injected from said second flexible duct through said communication, said external coating swells balloon-like for adapting itself to wall portions of the uterus horn thereby avoiding refluxes of liquids that have been introduced in said uterus horn when intrauterine fluids are being suctioned through said first flexible duct.

11. A device according to claim 10, wherein the first flexible duct and the second flexible duct are concentric, and said first flexible duct extends within said second flexible duct.

12. A device according to claim 1, further comprising an elastic small external coating provided on the outside of the probe at a portion near said distal end of the probe, and a communication between the longitudinal chamber and said outside of the probe, provided in said area near to the distal end of the probe, said external coating and said communication being arranged such that, when the distal end of the flexible probe has been placed in a final position in the uterus horn and air is injected from said longitudinal chamber through said communication, said external coating swells balloon-like for adapting itself to wall portions of the uterus horn thereby avoiding refluxes of liquids that have been introduced in said uterus horn when intrauterine fluids are being suctioned through said flexible duct.

13. A device according to claim 1, wherein the probe has a resilience such that, a longitudinal section of 5 cm length of the probe is able to bend 30° to 160°, and a consistency such that a longitudinal section of 8 to 10 cm length of the probe resists a load of 1.5 to 4.5N without bending when the load is applied perpendicularly on the longitudinal section.

14. A device according to claim 1, wherein the probe has a resilience such that, a longitudinal section of 5 cm length of the probe is able to bend 100° to 150, and a consistency such that a longitudinal section of 8 to 10 cm length of the probe resists a load of 1.5 to 4.5N without bending when the load is applied perpendicularly on the longitudinal section.

15. A device according to claim 1, wherein the probe has a resilience such that, a longitudinal section of 5 cm length of the probe is able to bend 135° to 145°, and a consistency such that a longitudinal section of 8 to 10 cm length of the probe resists a load of 1.5 to 4.5N without bending when the load is applied perpendicularly on the longitudinal section.

16. A device according to claim 1, wherein the flexible tubular body is a longitudinal helicoidal member and the outer surface of the probe is made of a layer of flexible material.

17. A device according to claim 1, wherein the flexible tubular body is made of a first flexible material and the outer surface of the probe is made of a layer of a second flexible material.

18. A device according to claim 1, wherein the surface of the probe is the surface of the flexible tubular body.

19. A method for introducing and/or collecting fluids in the inside of the uterus of an animal, the device for being introduced through a vagina, an entry of a cervix duct, and the cervix duct into a uterus horn of a uterus body, and comprising a tube having a proximal end and a distal end, and a probe axially and slidably extending through the tube, wherein the probe has a proximal end and a distal end, and comprises a flexible tubular body, at least one flexible duct having an inner space and fixedly housed inside the flexible tubular body, the flexible duct extending through a longitudinal chamber within the flexible body, and an outside surface, the probe having an equilibrium between consistency and resilience such that, when being pushed after emerging from the distal end of the tube, the distal end of the probe advances first through the cervix duct and thereafter through the uterus horn;

the method comprising a first step of introducing the tube through the vagina until reaching the cervix duct, a second step of rotating the tube is rotated counterclockwise making the tube advance and become anchored within the cervix duct, whereby a firm holding of the cervix duct by the tube being produced, a third step comprising introducing, by the proximal end of the tube, the distal end of the flexible probe until the distal end of the flexible probe reaches the distal end of the tube and then slightly rotating the tube to the left and to the right as well as simultaneously pushing the flexible probe until a first protuberance of the cervix duct is surpassed, a fourth step of further pushing the flexible probe until the distal end of the flexible probe surpasses protuberances of the cervix duct until reaching the uterus body, a fifth step of further pushing the flexible probe through the uterus horn until the distal end of the probe reaches an upper portion of uterus horn, and a sixth step of injecting the fluid through into said upper portion of the uterus horn.

20. A method according to claim 19, wherein the probe comprises coupling means for coupling a tap, the coupling means being provided at the proximal end of the probe for at least one of introducing and collecting fluids.

21. A method according to claim 19, wherein the proximal end of the tube comprises a widened portion to facilitate handling of the device.

22. A method according to claim 19, wherein the distal end of the tube has an external surface comprising a spiral portion that facilitates introduction and fixing of the tube in the entry of the cervix duct.

23. A method according to claim 22, wherein the intrauterine fluids contain embryos, said liquids being suctioned from an anterior third of the uterus body.

24. A method according to claim 19, wherein the device further comprises an elastic small external coating provided on the outside of the probe at a portion near said distal end of the probe, and a communication between the longitudinal chamber and said outside of the probe, provided in said area near to the distal end of the probe, said external coating and said communication being arranged such that, when the probe has been placed the upper portion of the uterus horn in the fifth step, the method comprises a first additional step of injecting air from said longitudinal chamber through said communication such that said external coating swells balloon-like for adapting itself to wall portions of the uterus horn thereby avoiding refluxes of liquids being introduced in said uterus horn when intrauterine fluids are being suctioned through said flexible duct.

25. A method according to claim 24, wherein the intrauterine fluids contain embryos, said liquids being suctioned from an anterior third of the uterus body.

26. A method according to claim 19, wherein the device further comprises the flexible duct as a first flexible duct an additional flexible as a second duct within the probe an elastic small external coating provided on the outside of the probe at a portion near said distal end of the probe, and a communication between the second flexible duct and said outside of the probe, provided in said area near to the distal end of the probe, said external coating and said communication being arranged such that, when the distal end of the flexible probe has been placed in the upper portion of the uterus horn in the fifth step, the method comprises a first additional step of injecting air from said second flexible duct through said communication such that said external coating swells balloon-like for adapting itself to wall portions of the uterus horn thereby avoiding refluxes of liquids being introduced in said uterus horn when intrauterine fluids are being suctioned through said first flexible duct.

27. A method according to claim 19, wherein the probe has a resilience such that, a longitudinal section of 5 cm length of the probe is able to bend 30° to 160°, and a consistency such that a longitudinal section of 8 to 10 cm length of the probe resists a load of 1.5 to 4.5N without bending when the load is applied perpendicularly on the longitudinal section.

28. A method according to claim 19, wherein the probe has a resilience such that, a longitudinal section of 5 cm length of the probe is able to bend 100° to 150, and a consistency such that a longitudinal section of 8 to 10 cm length of the probe resists a load of 1.5 to 4.5N without bending when the load is applied perpendicularly on the longitudinal section.

29. A method according to claim 19, wherein the probe has a resilience such that, a longitudinal section of 5 cm length of the probe is able to bend 135° to 145°, and a consistency such that a longitudinal section of 8 to 10 cm length of the probe resists a load of 1.5 to 4.5N without bending when the load is applied perpendicularly on the longitudinal section.

30. A method according to claim 19, wherein the flexible tubular body is a longitudinal helicoidal member and the outer surface of the probe is made of a layer of flexible material.

31. A method according to claim 19, wherein the flexible tubular body is made of a first flexible material and the outer surface of the probe is made of a layer of a second flexible material.

32. A method according to claim 13, wherein the surface of the probe is the surface of the flexible tubular body.

33. A probe for introducing and/or collecting fluids in the inside of the uterus of an animal, the probe for being introduced through a vagina, an entry of a cervix duct, and the cervix duct into a uterus horn of a uterus body, the probe having a proximal end and a distal end, and comprising a flexible tubular body, at least one flexible duct having an inner space and fixedly housed inside the flexible tubular body, the flexible duct extending through a longitudinal chamber within the flexible body, and an outside surface, the probe having an equilibrium between consistency and resilience such that its distal end of the flexible probe is capable of advancing first through the cervix duct and thereafter through the uterus horn.

34. A probe according to claim 33, wherein the probe has a resilience such that, a longitudinal section of 5 cm length of the probe is able to bend 30° to 160°, and a consistency such that a longitudinal section of 8 to 10 cm length of the probe resists a load of 1.5 to 4.5N without bending when the load is applied perpendicularly on the longitudinal section.

35. A probe according to claim 33, wherein the probe has a resilience such that, a longitudinal section of 5 cm length of the probe is able to bend 100° to 150, and a consistency such that a longitudinal section of 8 to 10 cm length of the probe resists a load of 1.5 to 4.5N without bending when the load is applied perpendicularly on the longitudinal section.

36. A probe according to claim 33, wherein the probe has a resilience such that, a longitudinal section of 5 cm length of the probe is able to bend 135° to 145°, and a consistency such that a longitudinal section of 8 to 10 cm length of the probe resists a load of 1.5 to 4.5N without bending when the load is applied perpendicularly on the longitudinal section.

37. A probe according to claim 33, wherein, between the flexible duct and the flexible tubular body of the probe, a plurality of flexible longitudinal ribs is arranged for increasing consistency and maintaining flexibility of the probe.

38. A probe according to claim 33, wherein the flexible longitudinal ribs are steel threads.

39. A probe according to claim 33, wherein the longitudinal chamber is tubular.

40. A probe according to claim 33, wherein the distal end of the probe comprises a distal piece that is adapted to the inner space of the flexible tubular body and to the flexible duct, the distal piece including an opening being located as a continuation of the flexible duct for establishing at least one of an inlet and an outlet for the fluid.

41. A probe according to claim 33, further comprising coupling means for coupling a tap, the coupling means being provided at the proximal end of the probe for at least one of introducing and collecting fluids.

42. A probe according to claim 33, further comprising coupling means for coupling a tap, wherein the coupling means for the tap is a proximal piece connected to the inner space of the flexible tubular body, to the flexible duct, and to the tap.

43. A probe according to claim 33, wherein the probe comprises said flexible duct as a first flexible duct an additional flexible duct within the probe, an elastic small external coating provided on the outside of the probe at a portion near said distal end of the probe, and a communication between the second flexible duct and said outside of the probe, provided in said area near to the distal end of the probe, said external coating and said communication being arranged such that, when the distal end of the flexible probe has been placed in a final position in the uterus horn and air is injected from said second flexible duct through said communication, said external coating swells balloon-like for adapting itself to wall portions of the uterus horn thereby avoiding refluxes of liquids that have been introduced in said uterus horn when intrauterine fluids are being suctioned through said first flexible duct.

44. A probe according to claim 43, wherein the first flexible duct and the second flexible duct are concentric, and said first flexible duct extends within said second flexible duct.

45. A probe according to claim 43, further comprising an elastic small external coating provided on the outside of the probe at a portion near said distal end of the probe, and a communication between the longitudinal chamber and said outside of the probe, provided in said area near to the distal end of the probe, said external coating and said communication being arranged such that, when the distal end of the flexible probe has been placed in a final position in the uterus horn and air is injected from said longitudinal chamber through said communication, said external coating swells balloon-like for adapting itself to wall portions of the uterus horn thereby avoiding refluxes of liquids that have been introduced in said uterus horn when intrauterine fluids are being suctioned through said flexible duct.

* * * * *